(12) United States Patent
Kulpakko et al.

(10) Patent No.: US 11,796,470 B2
(45) Date of Patent: Oct. 24, 2023

(54) METHOD FOR DETECTING A PROSTATE CANCER BIOMARKER

(71) Applicant: Aqsens Health Oy, Turku (FI)

(72) Inventors: Janne Kulpakko, Turku (FI); Jouko Vepsäläinen, Kuopio (FI); Susanna Paavilainen, Numminen (FI)

(73) Assignee: Aqsens Health Oy, Turku (FI)

( * ) Notice: Subject to any disclaimer, the term of this patent is extended or adjusted under 35 U.S.C. 154(b) by 80 days.

(21) Appl. No.: 17/307,039

(22) Filed: May 4, 2021

(65) Prior Publication Data

US 2021/0372989 A1 Dec. 2, 2021

(30) Foreign Application Priority Data

May 29, 2020 (EP) .................................... 20177435

(51) Int. Cl.
*G01N 21/64* (2006.01)
*G01N 33/84* (2006.01)
(Continued)

(52) U.S. Cl.
CPC ....... *G01N 21/6428* (2013.01); *A61B 5/4381* (2013.01); *G01N 21/78* (2013.01);
(Continued)

(58) Field of Classification Search
CPC ............... G01N 21/6428; G01N 33/84; G01N 2021/6439; G01N 33/582; G01N 33/57434
See application file for complete search history.

(56) References Cited

U.S. PATENT DOCUMENTS

2007/0292900 A1 12/2007 Frederickson et al.
2015/0004711 A1* 1/2015 Moore .................... G01N 33/20
436/81

FOREIGN PATENT DOCUMENTS

WO 2013126501 A1 8/2013
WO 2020089512 A1 5/2020

OTHER PUBLICATIONS

Kulpakko, J. et al. "Rapid time-resolved luminescence based screening of bacteria in urine with luminescence modulating biosensing phages," Analytical Biochemistry 570 (2019) 21-26, including Supplementary data; Available online Feb. 5, 2019. (Year: 2019).*

(Continued)

*Primary Examiner* — Jennifer Wecker
*Assistant Examiner* — Michelle Adams
(74) *Attorney, Agent, or Firm* — ZIEGLER IP LAW GROUP LLC

(57) ABSTRACT

The present disclosure relates to a method for detecting a prostate cancer related biomarker, including contacting the diluted sample with a modulating agent selected from a group consisting of sodium; 3-hydroxy-4-[(2-hydroxynaphthalen-1-yl)diazenyl]naphthalene-1-sulfonate, sodium; 3-hydroxy-4-[(1-hydroxynaphthalen-2-yl)diazenyl]-7-nitronaphthalene-1-sulfonate, triisopropylsilane, and iron(III) chloride, and a luminescent label to obtain a measurement sample. Then, the measurement sample is incubated for a period of time and excited thereafter. Time-resolved luminescence signal of the label in the measurement sample is measured, leading to an increased likelihood of prostate cancer of the human subject if the luminescence signal is at least 50% higher than for a control sample from a human subject without prostate cancer.

8 Claims, 3 Drawing Sheets

(51) Int. Cl.
*G01N 21/78* (2006.01)
*A61B 5/00* (2006.01)

(52) U.S. Cl.
CPC ..... *G01N 33/84* (2013.01); *G01N 2021/6439* (2013.01); *G01N 2800/7028* (2013.01)

(56) References Cited

OTHER PUBLICATIONS

European Patent Office, Extended European Search Report, Application No. 20177435.3, dated Sep. 25, 2020, 9 pages.
Pfrimer et al, "Impact of Aging on Urinary Excretion of Iron and Zinc", Libertas Academica, Nutrition and Metabolic Insights, pp. 47-50, DOI: 10.4137/NMI.S12977,2014, 4 pages, (Year: 2014).
Wang et al, "Iron Metabolism in Cancer", International Journal of Molecular Sciences, pp. 1-22, DOI:10.3390/jms20010095, 2019, 22 pages.
Ye Z et al, "Development of a novel terbium chelate-based luminescent chemosensor for time-resolved luminescence detection of instracellular Zn2+ ions" Biosensors and Bioelectronics, Elsevier Science Ltd. UK, Amsterdam, NL, vol. 26, No. 3, pp. 1043-1048, XP027393255, ISSN: 0956-5663, 6 pages, (Year: 2010).

\* cited by examiner

METHOD FOR DETECTING A PROSTATE CANCER BIOMARKER

FIELD

The present disclosure relates to a method for detecting prostate cancer related biomarkers from urine samples. The present disclosure also relates to a pre-screening method and kit usable at home as well as to a system for automatically analysing urine samples.

BACKGROUND

Prostate cancer is the most common cancer type for men. Overdiagnosis of prostate cancer may result in overtreatment. This causes often long-term side effects that impair the quality of life. The challenge is to separate the type of prostate cancer that grows very slowly and causes minimal harm from the aggressive metastatic prostate cancer types. Typical prostate cancer diagnosis covers methods of prostate specific antigen (PSA) detection, digital rectal examination, cystoscopy and magnetic resonance imaging (MRI). PSA detection is the easiest and the most cost-effective, as it can be measured from a blood sample in a laboratory. However, a drawback of PSA detection is that the amount of PSA in the blood can rise also from several other reasons e.g. in benign conditions and therefore the detection gives high false positive results. Such false positive results then lead to additional diagnosis and unnecessary treatments, not to mention mental stress. None of the above listed methods are suitable for the population level screening of prostate cancer.

SUMMARY

In view of the known diagnostic methods, there is a need for a cost-effective, simple, fast and reliable method of diagnosing aggressive prostate cancer. Advantageously, it is also aimed to provide a method for pre-screening prostate cancer at home, using a simple test kit. Still further, it is aimed to provide a system for automatic screening, that would be easy to implement.

A typical method for detecting a prostate cancer related biomarker comprises contacting a urine sample of a human subject with a modulating agent selected from a group consisting of sodium; 3-hydroxy-4-[(2-hydroxynaphthalen-1-yl)diazenyl]naphthalene-1-sulfonate, sodium; 3-hydroxy-4-[(1-hydroxynaphthalen-2-yl)diazenyl]-7-nitronaphthalene-1-sulfonate, triisopropylsilane, and iron(III) chloride, and a luminescent label to obtain a measurement sample;

incubating the measurement sample;

illuminating the measurement sample with excitation light; and measuring time-resolved luminescence signal of the label in the measurement sample and determining an increased likelihood of prostate cancer of the human subject if the luminescence signal is at least 50% higher than for a control sample from a human subject without prostate cancer.

Another typical method for pre-screening a prostate cancer related biomarker comprises contacting a urine sample of a human subject within a test tube, wherein the test tube comprises triisopropylsilane and sodium; 3-hydroxy-4-[(2-hydroxynaphthalen-1-yl)diazenyl] naphthalene-1-sulfonate;

incubating the test tube with the sample; and visually observing the test tube and determining an increased likelihood of prostate cancer if a change of colour in the test tube content is observed A typical kit of parts comprises a test tube comprising triisopropylsilane and sodium; 3-hydroxy-4-[(2-hydroxynaphthalen-1-yl)diazenyl]naphthalene-1-sulfonate;

means for taking a urine sample; and means for contacting the diluted urine sample with the test tube.

A typical system for automatically analysing urine samples is connectable to a toilet bowl and comprises at least one detection device configured to receive a urine sample, to detect an initial colour of the urine sample, to contact the urine sample with modulating agents to form a measurement sample, to incubate the measurement sample and to detect a colour and/or intensity of the colour after incubation;

a computing device configured to analyse the detected colour and optional colour intensity, and to send information of any detected increased risk of prostate cancer; and means for communicating the detected colours and optional colour intensity to the computing device.

DETAILED DESCRIPTION

Figure 1:
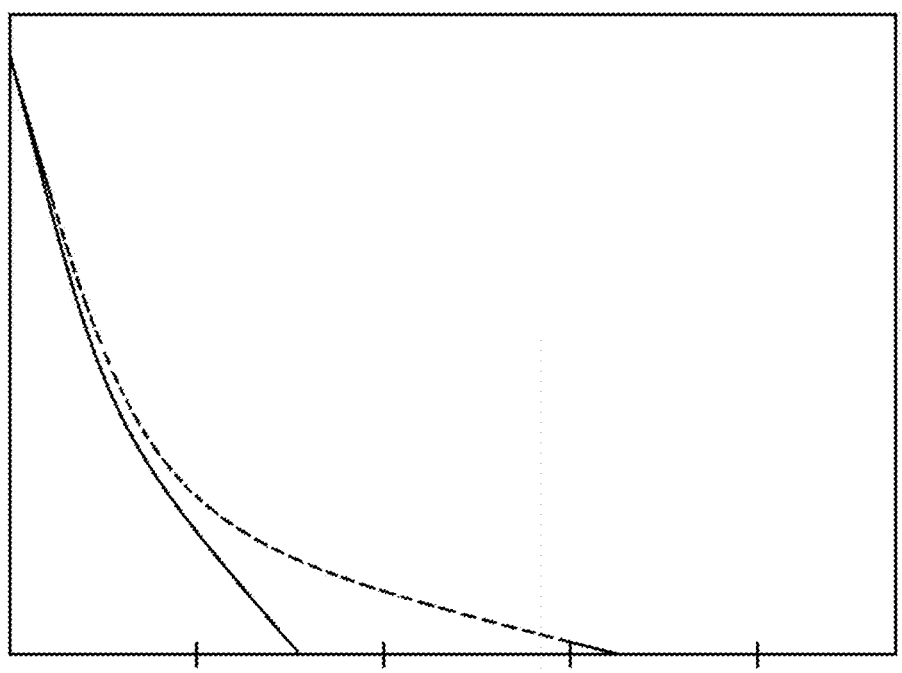
FIG. 1 illustrates results of an experiment.
Figure 2A:
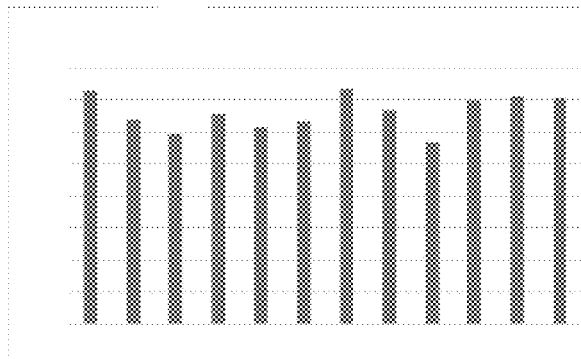
FIG. 2A-2F illustrate further results of experiments.
Figure 2B:
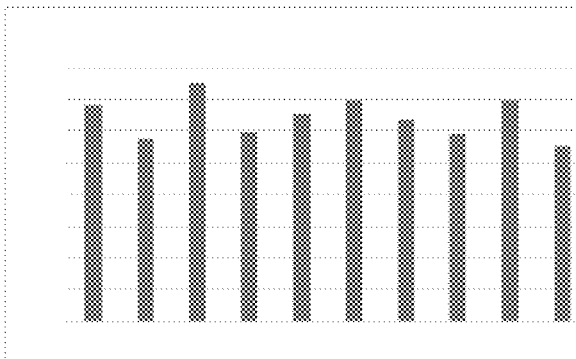
Figure 2C:
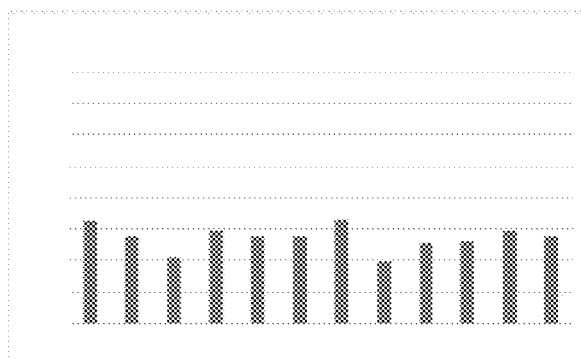
Figure 2D:
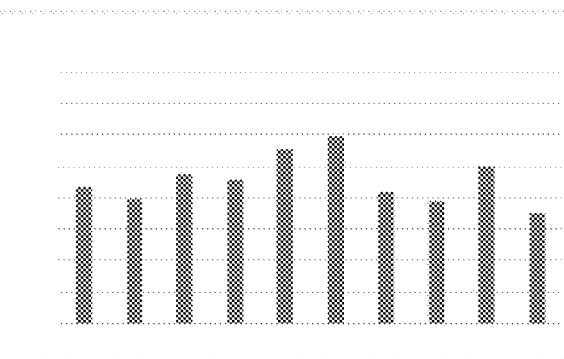
Figure 2E:
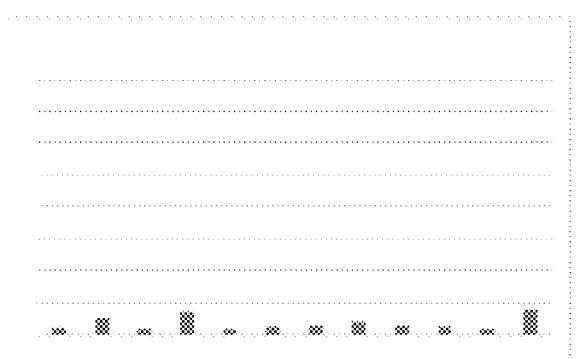
Figure 2F:
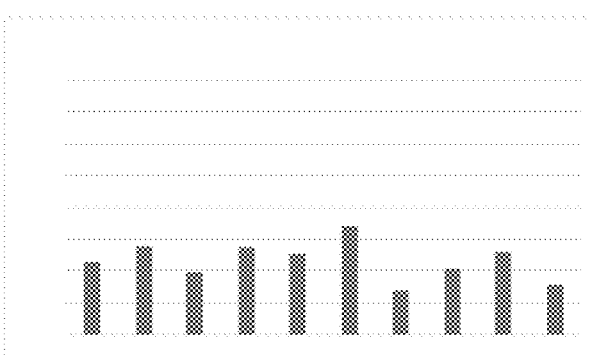

A method for detecting a prostate cancer related biomarker according to an embodiment comprises contacting a urine sample of a human subject with a modulating agent selected from a group consisting of sodium; 3-hydroxy-4-[(2-hydroxynaphthalen-1-yl)diazenyl] naphthalene-1-sulfonate, sodium; 3-hydroxy-4-[(1-hydroxynaphthalen-2-yl)diazenyl]-7-nitronaphthalene-1-sulfonate, triisopropylsilane, and iron(III) chloride, and a luminescent label to obtain a measurement sample;

incubating the measurement sample;

illuminating the measurement sample with excitation light; and measuring time-resolved luminescence signal of the label in the measurement sample and determining an increased likelihood of prostate cancer of the human subject if the luminescence signal is at least 50% higher than for a control sample from a human subject without prostate cancer.

The present disclosure thus provides a cost-effective yet reliable and quick method for pre-screening and early detection of malignant changes related to prostate cancer, as it allows to detect prostate cancer related biomarkers, as is demonstrated below in the Experimental part. For the time being, it is believed that the accuracy of this test method is at least 70-80%, while the accuracy of the common PSA testing mentioned above is significantly lower. Thus, the number of false positives is significantly reduced compared to the conventional method. The accuracy of the method is thus high and the test is reliable.

Preparation of a sample for the present method takes less than 5 minutes, while the test itself takes about 10 minutes. Thus, the method is efficient to use, and does not require any blood sample, which decreases further the cost of the testing, as less health care personnel is needed.

It is also believed that the present method may provide more information about the early benign changes that may lead to the cancer development. Indeed, as this is a pre-screening method, which is easy to use and can be used also at home (see below), with a high accuracy, it may allow to monitor patients more easily, to detect the changes that may cause trouble later. The present method can, in addition to pre-screening, also be used in cancer research including cellular and genetic research systems.

It is believed that the present method is based on a connection between cancer and iron metabolism. This connection is known but its role in cancer physiology is unknown (Wang Y, Yu L, Ding J, Chen Y. Iron Metabolism in Cancer. Int J Mol Sci. 2018; 20(1):95.). Urine iron concentration is typically between 50-100 μg/L with variation according to individual physiology and age (Pfrimer, Karina et al. "Impact of aging on urinary excretion of iron and zinc" Nutrition and metabolic insights (2014) vol. 7; 47-50.26.). The present method is based on the differences of iron binding molecules in the urine samples of healthy and unhealthy subjects. Indeed, these molecules are more abundant in cancer samples than in healthy samples. This difference is detected by the described method. It is assumed that both cancerous and healthy samples have the same concentration of iron, but different amounts of iron binders. Therefore, the signal is higher in cancerous cases as free iron is taken by binders. In a healthy sample, iron remains in the sample and interferes with the label causing a decrease of luminescence signal.

The modulating agent sodium; 3-hydroxy-4-[(2-hydroxynaphthalen-1-yl)diazenyl]naphthalene-1-sulfonate is sold under the trade name of Calcon™ (CAS number 2538-85-4) and the modulating agent sodium; 3-hydroxy-4-[(1-hydroxynaphthalen-2-yl)diazenyl]-7-nitronaphthalene-1-sulfonate is sold under the trade name of Eriochrome® Black T (CAS number 1787-61-7). Iron(III) chloride is preferably used in a purity of 97% (CAS number 7705-08-) and triisopropylsilane preferably in a purity of 98% (CAS number 6485-79-6).

When sodium; 3-hydroxy-4-[(2-hydroxynaphthalen-1-yl)diazenyl]-naphthalene-1-sulfonate is used as the modulating agent, it is typically used in an amount of 50-800 μM, most typically 250 μM in a volume of 4 μl. Sodium; 3-hydroxy-4-[(1-hydroxynaphthalen-2-yl)diazenyl]-7-nitronaphthalene-1-sulfonate, when used as the modulating agent, is typically used in an amount of 50-1000 μM, preferably 500 μM in a volume of 4 μl. When triisopropylsilane is used as the modulating agent, it is typically used in an amount of 4 μl of 10% solution, but also a solution of 2-25% can be used. Iron(III) chloride, when used as the modulating agent, is typically used in an amount of 5-500 μM, preferably 300 μM.

In the present method, if the luminescence signal is at least 50% higher than for a control sample from a human subject without prostate cancer, an increased likelihood of prostate cancer of the human subject is determined. The luminescence signal can thus be at least 50, 75, 90, 100, 125, 150, 175, 200, 250 or 300% higher than for a control sample, or even higher than this.

Typically, the present methods do not comprise a step that is practiced on a human body.

The label used can be europium chloride ($EuCl^{3+}$) label or a terbium chloride ($TbCl^{3+}$) label. These labels exist as complexes, as is known to a person skilled in the art. For example, europium(III) chloride, 99.99%, CAS Number 10025-76-0, from Sigma-Aldrich and terbium(III) chloride, 99.99%, CAS Number 10042-88-3, from Sigma-Aldrich can be used. The europium chloride label can be used for example as a complex of europium chloride, nitrilotriacetic acid (NTA) (for example 99%, CAS Number 139-13-9, from Sigma-Aldrich) and trioctylphosphine oxide (TOPO) (for example 99%, CAS Number 78-50-2, from Sigma-Aldrich). One possible combination is these three components in a 3:9:9 ratio. Instead of NTA, also 2-thenoyltrifluoroacetone (for example 99%, CAS Number 326-91-0, from Sigma-Aldrich) or 4,4,4-trifluoro-1-(2-furyl)-1,3-butanedione (for example 99%, CAS Number 326-90-9, from Sigma-Aldrich can be used.

The concentrations of the various components of a complex of europium chloride 80 nM-5.0 μM for the europium chloride; 5 nM-3 μM for TOPO and; 100 nM-3 μM for NTA. The concentration of europium chloride can thus be for example from 80 nM, 100 nM, 200 nM, 300 nM, 400 nM, 500 nM, 600 nM, 700 nM, 800 nM, 900 nM, 1 μM, 1.5 μM, 2 μM, 2.5 μM, 3 μM, 3.5 μM or 4 μM up to 200 nM, 300 nM, 400 nM, 500 nM, 600 nM, 700 nM, 800 nM, 900 nM, 1 μM, 1.5 μM, 2 μM, 2.5 μM, 3 μM, 3.5 μM, 4 μM, 4.5 μM or 5 μM. The concentration of TOPO can be for example from 5 nM, 10 nM, 15 nM, 20 nM, 25 nM, 30 nM, 35 nM, 40 nM, 45 nM, 50 nM, 55 nM, 60 nM, 65 nM, 70 nM, 75 nM, 80 nM, 100 nM, 200 nM, 300 nM, 400 nM, 500 nM, 600 nM, 700 nM, 800 nM, 900 nM, 1 μM, 1.5 μM or 2 μM up to 15 nM, 20 nM, 25 nM, 30 nM, 35 nM, 40 nM, 45 nM, 50 nM, 55 nM, 60 nM, 65 nM, 70 nM, 75 nM, 80 nM, 100 nM, 200 nM, 300 nM, 400 nM, 500 nM, 600 nM, 700 nM, 800 nM, 900 nM, 1 μM, 1.5 μM, 2 μM, 2.5 μM or 3 μM. The concentration of NTA can be for example from 100 nM, 200 nM, 300 nM, 400 nM, 500 nM, 600 nM, 700 nM, 800 nM, 900 nM, 1 μM, 1.5 μM or 2 μM up to 200 nM, 300 nM, 400 nM, 500 nM, 600 nM, 700 nM, 800 nM, 900 nM, 1 μM, 1.5 μM, 2 μM, 2.5 μM or 3 μM.

According to an embodiment, the label is used in an amount of 4 μl per microtiter well. One possibility is thus to use the label in an amount of 4 μL of label mixture containing europium chloride 0.717 μM, trioctylphosphine oxide 0.430 μM and nitrilotriacetic acid 0.430 μM (NTA) in dimethyl sulfoxide.

The excitation light can be for example from a pulsed laser, a light emitting diode (LED), or xenon-flash lamp.

According to an embodiment, the time-resolved luminescence signal is measured for a time of 200-800 μs after a 200-800 μs delay time. The signal can thus be measured for example for a time of from 200, 250, 300, 350, 400, 450, 500, 550, 600, 650, 700 or 750 μs up to 250, 300, 350, 400, 450, 500, 550, 600, 650, 700, 750 or 800 μs. Independently thereof, the delay time can be for example from 200, 250, 300, 350, 400, 450, 500, 550, 600, 650, 700 or 750 μs up to 250, 300, 350, 400, 450, 500, 550, 600, 650, 700, 750 or 800 μs.

The urine sample is optionally diluted before contacting the sample with the modulating agent. The diluent and the modulating agent can also be added simultaneously. The diluent can be for example physiological saline solution. The dilution rate can be for example 1:5-1:20. A dilution rate of 1:5 means that there is volume one part of the sample and 5 volume parts of the physiological saline solution. The dilution rate can be for example from 1:5, 1:6, 1:7, 1:8, 1:9, 1:10, 1:11, 1:12, 1:13, 1:14, 1:15 or 1:16 up to 1:7, 1:8, 1:9, 1:10, 1:11, 1:12, 1:13, 1:14, 1:15, 1:16, 1:17, 1:18, 1:19 or 1:20.

A typical incubation time is 1-15 minutes. A longer incubation time may decrease the efficiency of the method. The incubation time can be for example from 1, 2, 3, 4, 5, 6, 7, 8, 9, 10, 11 or 12 minutes up to 4, 5, 6, 7, 8, 9, 10, 11, 12, 13, 14 or 15 minutes. Incubation is usually done at room temperature and in a normal atmosphere.

The present disclosure also relates to another method, namely to a method for pre-screening a prostate cancer related biomarker, comprising contacting a urine sample of a human subject within a test tube, wherein the test tube comprises triisopropylsilane and sodium; 3-hydroxy-4-[(2-hydroxynaphthalen-1-yl)diazenyl]naphthalene-1-sulfonate;

incubating the test tube with the sample; and visually observing the test tube and determining an increased likelihood of prostate cancer if a change of colour in the test tube content is observed This method is thus related to a test that a subject can do at home. The embodiments and variants disclosed above in connection with the method using a label apply mutatis mutandis to this home-method, unless otherwise indicated.

Most typically, if dilution of the sample is used, the urine sample is diluted to 1:2 (1 part of sample, 2 parts of physiological saline solution). The two modulating agents are arranged in the sample tube. In case the sample contains cancerous markers, the colour will change in the test tube, to a colour visible in the range of 630-650 nm, i.e. the test tube will turn red/dark red. For a healthy subject, there is no change of colour. It is to be noted that even if the sample is then dried, the colour remains in the test tube.

The change of colour can be observed visually by the human eye, or it can be read for example with a specific app loaded on a mobile phone and used together with a camera of the mobile phone.

The volume of the test tube is typically 1-10 ml, for example 3 ml. Dilution of the sample is preferably done in the test tube. In this method, the incubation time is also typically 1-15 minutes, and the variants listed above apply mutatis mutandis. According to an embodiment, the triisopropylsilane is used in an amount of for 3 mL sample, preferably 200 µl of a 10% solution for a diluted sample volume of 3 ml. The triisopropylsilane can also be used as a 5-25% solution. Sodium; 3-hydroxy-4-[(2-hydroxynaphthalen-1-yl)diazenyl]naphthalene-1-sulfonate is used in an amount of 200 µL of 250 µM solution for a diluted sample volume of 3 ml. This modulating agent can also be used in a range of 100-800 µM.

The present disclosure still further relates to kit of parts comprising a test tube comprising triisopropylsilane and sodium; 3-hydroxy-4-[(2-hydroxynaphthalen-1-yl)diazenyl]naphthalene-1-sulfonate;

means for taking a urine sample; and means for contacting the diluted urine sample with the test tube.

The kit of parts is thus usable for testing for example at home, although it could also be used in health care, especially in places with less or no laboratory equipment. The kit of parts may also contain some physiological saline solution for the dilution, for example in the form of an ampoule. The kit of parts may then still further contain means for diluting the urine sample.

The means for taking a urine sample may be a sterile cup and a sterile syringe. The means for diluting the urine sample may comprise a sterile cuvette or tube, made from transparent material and having markings showing the user how much of the physiological saline is to be added. The means for contacting the diluted urine sample with the test tube may be for example a pipette. The kit preferably also includes use instructions.

This disclosure still further relates to a kit comprising a modulating agent and instructions of using it together with a time-resolved luminescence measuring apparatus, i.e. instructions for carrying out the method for determining likelihood of prostate cancer. The kit may also comprise either a database of control samples, an access to such database, or a number of control samples to be used for the comparison. Additionally, the kit may comprise the label.

The present disclosure also relates to a use of sodium; 3-hydroxy-4-[(2-hydroxynaphthalen-1-yl)diazenyl]naphthalene-1-sulfonate, sodium; 3-hydroxy-4-[(1-hydroxynaphthalen-2-yl)diazenyl]-7-nitronaphthalene-1-sulfonate, triisopropylsilane, or iron(III) chloride in pre-screening of prostate cancer. The use is typically ex vivo.

The present disclosure still further relates to a system for automatically analysing urine samples, which system is connectable to a toilet bowl. The system comprises at least one detection device configured to receive a urine sample, to detect an initial colour of the urine sample, to contact the urine sample with modulating agents to form a measurement sample, to incubate the measurement sample and to detect a colour and/or intensity of the colour after incubation;

a computing device configured to analyse the detected colour and optional colour intensity, and to send information of any detected increased risk of prostate cancer; and means for communicating the detected colours and optional colour intensity to the computing device.

The detection device can be attached to the inside of a toilet bowl, for example on the front part and/or the rear part of the toilet bowl, such that it is possible to provide a urine sample when urinating. For example, when two detection devices are used, they can be configured to wake up once a urine sample is received, and thus to communicate only when active (or woken up). The detection device is preferably attachable by removable attachment means, which do not require drilling or similar. The detection device may also be made integral to the toilet bowl.

The means for communicating the detected colours and/or colour intensities to the computing device can be for example via radio communication or similar. The computing device may also be connected, for example via a communication network, to a server system, in which case the server system can do the analysis and further actions based on any detected information indicating an increased risk of prostate cancer. The server can also be configured to store any information provided.

The analysis of the detected colour and optional colour intensity includes comparing the colour detected before addition of the modulating agents to the colour or the intensity of the colour after incubation. It is also possible to detect the colour immediately after addition of the modulating agents, in which case both detections are based on the intensity of the colour. The result of this comparison is then compared to results stored in a database, i.e. a database of results from samples of persons not having prostate cancer and results from samples of persons having prostate cancer. The result of this latter comparison, at least when indicating an increased risk of prostate cancer, is then communicated further.

The detection device can also be configured to dilute the sample, for example with water coming from the toilet's water system.

The detection device can have for example the following structure. It contains an opening for receiving the urine sample, and the opening is connected to the first part of a fluid system. In this first part, also water is added to the sample, typically from the toilet's water system, to form a diluted sample. The first part is at least partially transparent, so that a sensor can see the diluted sample. The sensor can be for example a camera or a photodetector such as a photosensitive diode arranged to measure the colour and/or intensity of light between 620-650 nm. The sensor thus reads the colour of the diluted sample after formation of the diluted sample, typically within seconds, and communicates the measurement results to the computing device. Thereafter, the diluted sample is contacted with a mixture of modulating agents (as disclosed above in connection with the test method that can be carried out at home), and incubated for 1-10 minutes, for example for 5 minutes. During this time, the opening is closed so as not to allow any more fluids to enter the detection device. This can happen either in the same part as the dilution, or in a different part. After incubation, the sample can either again remain in the same part where dilution took place, or be moved to another part of the fluid system. In case it is moved, the system may comprise a second sensor, or if the sample remains all the time in the same space, the first sensor is used again, to measure the colour and/or intensity of the light emitted at 620-650 nm. Again, the results are communicated to the computing device, which then makes an analysis (or send the information further to a server for example), and if need be, sends an alert for example to a mobile device of the user of the toilet.

Experimental Part

Urine samples from subjects known to be healthy and from subjects known to suffer from prostate cancer were tested as follows.

Preliminary experiments were carried out using 10 cancer and 12 healthy urine samples from human subjects. Prior to further steps, the samples were centrifuged 10000 rpm for 5 min to remove any excess solid material. 1 ml of clear supernatant was diluted to 9 ml of physiological salt solution.

First 4 µl of modulating agent solution was added to the microtiter wells. The modulating agent consisted of one of four different aforementioned modulating agents in MQ water. All the modulating agents were obtained from Sigma-Aldrich. Next, each sample was divided in three parallel samples of 100 µl volume and pipetted to a 96 well plate.

Finally, 4 µl of a label mixture containing europium chloride 0.717 µM, trioctylphosphine oxide (TOPO) 0.430 µM and nitrilotriacetic acid 0.430 µM (NTA) in dimethyl sulfoxide (DMSO) was added to each microtiter well.

After 10 minutes of incubation, luminescence emission intensities were measured in a 400 µs window after a 400 µs delay time using a Victor 2 multilabel counter (Wallac, Perkin-Elmer Life and Analytical Sciences).

FIG. 1 illustrates the time-resolved luminescence signal of a sample from a healthy subject and of a subject with cancer. The time-resolved luminescence is given on ordinate and time on abscissa. The full line illustrates the result for a sample from a healthy subject ("normal" sample), and the dashed line for a sample from a subject having prostate cancer. There is thus a clear difference in the luminescence, especially after a certain time.

FIGS. 2A-2F show the luminescence signal of samples from healthy subjects and from subjects with cancer, at different points of time, height of the bar indicating the luminescence. The number of samples tested was 12 for healthy subjects (FIGS. 2A, 2C and 2E) and 10 for samples of subjects with cancer (FIGS. 2B, 2D and 2F), each vertical bar representing one sample. At time 0, the reagents listed above were added to the samples, and luminescence was measured at times 0 minutes (FIGS. 2A and 2B), 5 minutes (FIGS. 2C and 2D) and 10 minutes (FIGS. 2E and 2F), i.e. immediately or after 5 or 10 minutes of incubation. Measurement at the time point 5 minutes indicates that healthy samples have faster reduction of signal level than cancer samples. After 10 minutes of incubation, signal difference is already remarkable and sufficient for diagnostic purposes.

Figure 3A:
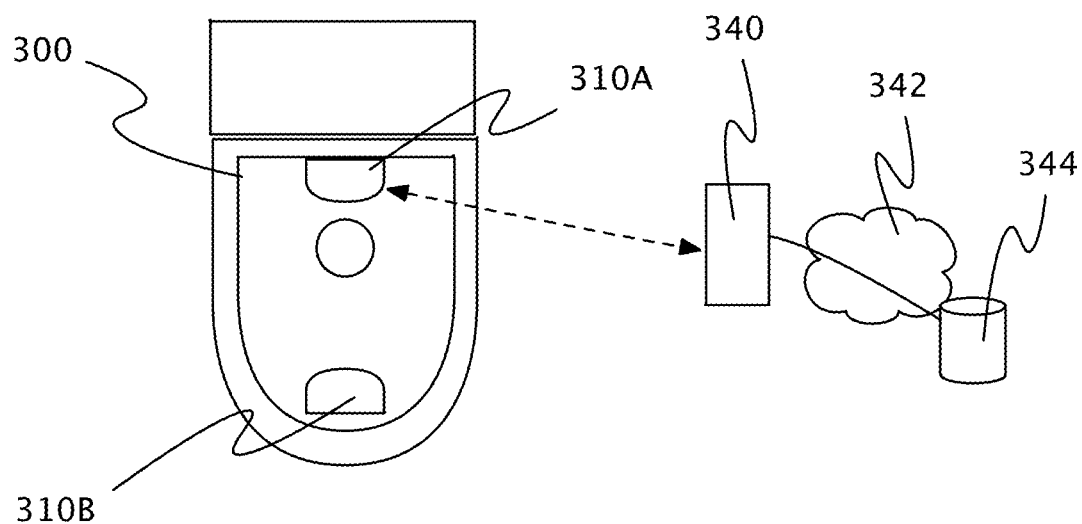
FIGS. 3A and 3B are schematic illustrations of an example system for detecting prostate cancer.

FIG. 3A is a schematic illustration of a toilet 300 as seen from above. A detection device 310A is attached on a backside of the toilet 300, inside the toilet bowl, and a second detection device 310B is attached on a frontside of the toilet 300, inside the toilet bowl. The detection devices 310A, 310B are attached in such a way that it is possible to provide urine samples when urinating. The detection devices 310A, 310B are connected via a radio communication to a computing device 340. The computing device 340 is in turn connected via a communication network 342 to a server system 344. The detection device is configured to measure a visual signal from the urine sample and to send the measurement results to the server system 344 for further analysis and storage.

Figure 3B:
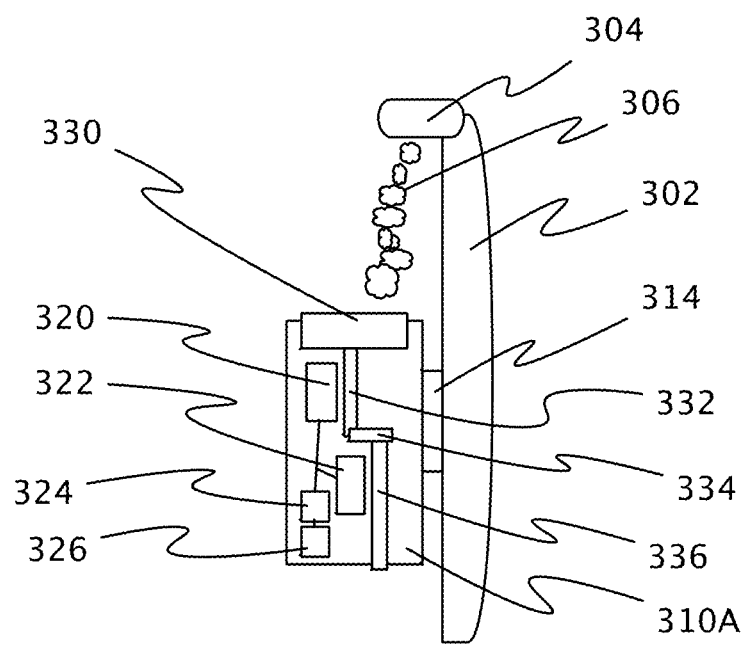

FIG. 3B is an illustration of details of the detection device 310A when in use. The detection device 310A is attached to a side 302 of the toilet with attachment means 314. The detection device 310A comprises a first opening 330 for receiving the urine sample as well as receiving water 306 from a water output 304 to dilute the sample. The urine sample and water are led from the first opening 330 to a first portion 332 of a fluid channel. The first portion 332 is at least partly transparent for a first sensor 320 to measure the first colour of the diluted sample and provide the measured first colour of the sample to a controller 324. The diluted sample is further directed via a second portion 334 of the fluid system to a third portion 336 of the fluid system. The modulating agents are also fed to the third portion 336 (not shown). The third portion 336 is configured to maintain the diluted sample together with the modulating agents for incubation. The third portion is at least partly transparent for a second sensor 322 to measure a second colour and/or its intensity and provide the measured second colour and/or intensity to the controller 324. The controller is connected to a communication module 326, and the communication module 326 provides measurement results to the computing device 340 as shown in FIG. 3A.

The invention claimed is:

1. A method for detecting a prostate cancer related biomarker, comprising diluting a urine sample of a human subject in a physiological saline solution to obtain a diluted sample, wherein the urine sample is diluted using a dilution ratio of 1:5-1:20 urine sample to physiological saline;

contacting the diluted urine sample with a luminescent label and a modulating agent selected from a group consisting of sodium;3-hydroxy-4-[(2-hydroxynaphthalen-1-yl)diazenyl]naphthalene-1-sulfonate, sodium; 3-hydroxy-4-[(1-hydroxynaphthalen-2-yl)diazenyl]-7-nitronaphthalene-1-sulfonate, triisopropylsilane, and iron(III) chloride to obtain a measurement sample;

incubating the measurement sample;

illuminating the measurement sample with excitation light; and measuring a time-resolved luminescence signal of the luminescent label in the measurement sample, and determining an increased likelihood of prostate cancer of the human subject if the time-resolved luminescence signal is at least 50% higher than for a control sample from a human subject without prostate cancer.

2. The method according to claim 1, wherein the luminescent label is selected from europium chloride and terbium chloride.

3. The method according to claim 1, wherein the time-resolved luminescence signal is measured for a time of 200-800 us after a 200-800 us delay time.

4. The method according to claim 1, wherein the modulating agent is sodium;3-hydroxy-4-[(2-hydroxynaphthalen-1-yl)diazenyl]naphthalene-1-sulfonate, in an amount of 4 µL of a 50-800 µM solution.

5. The method according to claim 1, wherein the modulating agent an amount of 4 µL of a 50-1000 µM solution.

6. The method according to claim 1, wherein the modulating agent is triisopropylsilane, in an amount of 4 µL of a 2-25% solution.

7. The method according to claim 1, wherein the modulating agent is iron(III) chloride.

8. The method according to claim 1, wherein an incubation time is 1-15 minutes.

\* \* \* \* \*